(12) United States Patent
Luo

(10) Patent No.: US 8,718,230 B2
(45) Date of Patent: May 6, 2014

(54) METHOD AND SYSTEM FOR DETERMINING THE CONSTITUENT CONTENT OF A MULTIPHASE FLUID

(76) Inventor: Pingan Luo, Beijing (CN)

(*) Notice: Subject to any disclaimer, the term of this patent is extended or adjusted under 35 U.S.C. 154(b) by 366 days.

(21) Appl. No.: 12/991,170

(22) PCT Filed: Jan. 21, 2009

(86) PCT No.: PCT/CN2009/070253
§ 371 (c)(1),
(2), (4) Date: Aug. 2, 2011

(87) PCT Pub. No.: WO2009/135390
PCT Pub. Date: Nov. 12, 2009

(65) Prior Publication Data
US 2012/0020458 A1    Jan. 26, 2012

(30) Foreign Application Priority Data
May 6, 2008    (CN) .......................... 2008 1 0097203

(51) Int. Cl.
*G01N 23/12*    (2006.01)
(52) U.S. Cl.
USPC .............................................. 378/53; 378/51
(58) Field of Classification Search
None
See application file for complete search history.

(56) References Cited

U.S. PATENT DOCUMENTS

| | | | |
|---|---|---|---|
| 4,618,975 A | | 10/1986 | Glantschnig |
| 4,788,852 A | * | 12/1988 | Martin et al. ................ 73/61.44 |
| 5,014,288 A | | 5/1991 | Chase et al. |
| 6,097,786 A | * | 8/2000 | Groves et al. .................. 378/53 |
| 6,600,805 B2 | | 7/2003 | Hansen |
| 2007/0291898 A1 | * | 12/2007 | Groves et al. .................. 378/51 |
| 2010/0172470 A1 | * | 7/2010 | Kuwabara ....................... 378/53 |

FOREIGN PATENT DOCUMENTS

| | | |
|---|---|---|
| CN | 101101268 A | 1/2008 |
| CN | 101261235 A | 9/2008 |
| JP | 2007-218845 A | 8/2007 |

* cited by examiner

*Primary Examiner* — Hoon Song
*Assistant Examiner* — Danielle Fox
(74) *Attorney, Agent, or Firm* — Gottlieb, Rackman & Reisman, P.C.

(57) ABSTRACT

A method for determining the constituent content of a multiphase fluid includes the following steps: x-rays at single-energy or dual-energy levels are produced by an x-ray machine, after said x-rays pass through the multiphase fluid, the data at each energy level are detected by a detector sub-system which is composed of one or two detectors, and the mass percents of the components in the multiphase fluid are calculated by a controlling and data processing sub-system based on the detected data. Said multiphase fluid is a two-phase or three-phase mixture in crude oil or natural gas. The method can be used for automatic online measurement of the production in oil and gas fields.

14 Claims, 7 Drawing Sheets

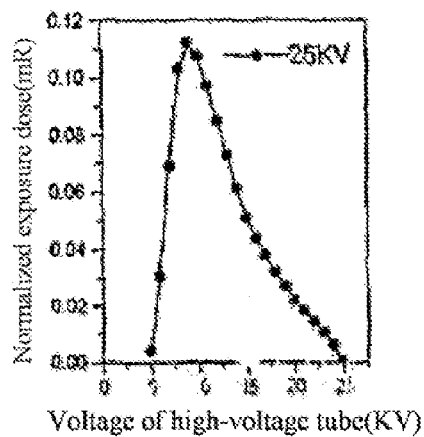
Figure 1-1
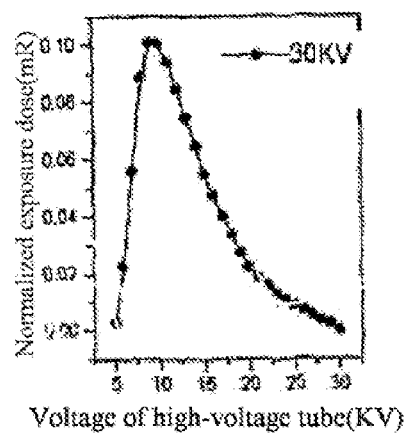
Figure 1-2
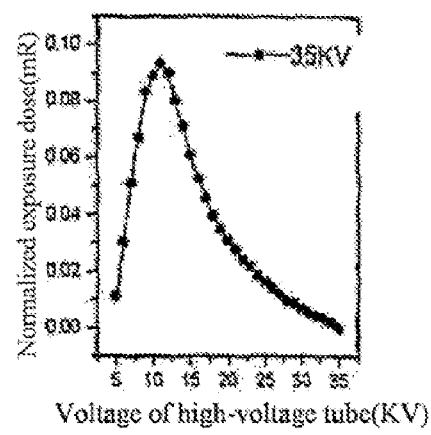
Figure 1-3
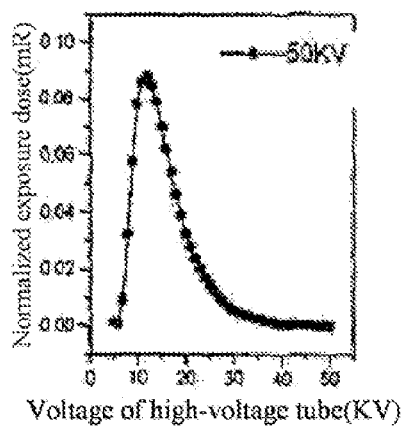
Figure 1-4
Figure 1

METHOD AND SYSTEM FOR DETERMINING THE CONSTITUENT CONTENT OF A MULTIPHASE FLUID

TECHNICAL FIELD

The invention relates to the technical field of petroleum measurement and specifically relates to a system for measuring the water content, the oil content, the gas content or the sand content in the production of crude oil and natural gas, in particular to a dual-energy x-ray measurement technology which utilizes the action principle of x-rays produced by an x-ray machine with components to measure the indexes, such as the water content, the oil content, the gas content or the sand content, in oil and gas transportation pipelines under the condition of coexistence of three-phase media of oil-water-gas, oil-sand-water or gas-sand-water during the production of oil and gas fields (which can only measure three indexes related with the corresponding mixed fluid in the four indexes), belonging to the technical field of international patent classification G01N.

BACKGROUND ARTS

Crude oil and natural gas are taken as one of the most important energies as a whole, and the crude oil and the natural gas exploited from oil and gas wells form a mixture composed of multiphase media of oil, water, natural gas or sand and the like. The treatment of the mixture firstly needs to carry out gas-liquid separation, the remaining oil-water mixed liquid is dehydrated, and then a finished oil or natural gas product with very low water content is obtained for outward transportation or selling. It is necessary to monitor and separate the sand contained therein, otherwise, equipment is easy to be damaged. In a series of production activities, such as dehydration treatment of the crude oil or the natural gas and the like, it is necessary to timely and accurately grasp the water content, the gas content or the oil content and the like of the crude oil, thereby facilitating the control of the production process and ensuring the production of the qualified finished oil or natural gas product. Therefore, the indexes, such as the water content, the gas content, the oil content or the sand content in the crude oil or the natural gas, constitute a group of important parameters during the collection, the smelting and the transportation processes of petroleum and natural gas in the petrochemical industry. The water injection oil production process is mainly adopted at present, in particular to many old oil fields, and the water content in the produced crude oil is generally higher. Thus, the accurate detection of the water content, the gas content, the oil content or the sand content in the crude oil or the natural gas plays the important role in the production and the trade of the crude oil or the natural gas.

At present, in the production of the crude oil, the main methods for measuring the water content in the crude oil are as follows: artificial distillation assay method, microwave method (or radio frequency method), capacitance method, short-wave method, thermal conduction method, vibration densitometer method and γ-ray method. 1. The microwave method (such as CN1112677) is as follows: according to the situation that electromagnetic waves are interacted with dielectric components, the dissipation is related with the size and the relative dielectric constant of the components, and the different dielectric constants of oil and water can cause different radio frequency impedance properties presented by the measured objects, when a radio frequency signal is transmitted to a capacitive radio frequency sensor taking an oil-water mixture as a medium, the load impedance changes along with the change of oil-water ratio of the mixed medium, that is when the water content in the crude oil changes, the wave parameter changes therewith, thereby realizing the measurement of the water content; 2. the capacitance method (such as CN1186236) is as follows: according to the situation that the different dielectric constants of the oil and water reflect different capacitances of a capacitor constituted by a polar plate, the measurement of the change of the capacitance can be used for measuring the change of the water content; 3. the short-save method (such as CN2349574) is as follows: a (rear) probe is utilized to transmit a 3.579 MHz short-save signal into the crude oil, the current state of the crude oil is checked up, after a few seconds, the 3.579 MHz short-save signal is further transmitted into the crude oil through another (front) probe, the water-containing signal in the oil is taken out, then the difference between the two measured values is got, and the instantaneous water content can be obtained after the treatment; 4. the thermal conduction method (such as CN1259671) utilizes the differences in thermophysical properties of a liquid-liquid two-phase fluid, such as thermal conduction, specific heat, viscosity and the like, and simultaneously measures the water content in the crude oil and the oil-water flow rate; 5. the vibration densitometer method (such as CN1789969, CN2359692) utilizes a liquid level measurement element to measure the liquid level of the crude oil in an oil storage tank (or a separator), and utilizes a pressure measurement instrument to measure the pressure of the part without the crude oil and the pressure of the bottom part in the oil storage tank (or the separator); and 6. the ray method (such as CN86105543A, CN2359692Y, CN1086602A, CN2383068Y) works according to the principle that when γ rays pass through different media, the attenuation is different. The various measurement methods other than the γ-ray method belong to the Contact type measurement; as the crude coil has strong causticity and serious scale formation and wax formation, the reliability of long-term running of the instruments is poor, particularly, the instruments can not eliminate the influences on the measurement of the water content caused by the contained gas, thereby causing the greater measurement error. In this regard, the patents of CN2452022Y, CN2646704Y and CN2646705Y specially design different erasers to erase the impurities accumulated on the outside of sensors. In addition, the water content change measured by the capacitance method, the radio frequency method and the microwave method is in non-linear relationship with the measured objects, an inflection point exists in a certain range of the water content, and the crude oil is the oil-water-gas mixture and has variable physical and chemical properties, so that the above measurement methods other than the γ-ray method can not well meet the production requirements during the actual applications.

A crude oil water content analyzer which works according to the law of interaction between the γ-rays and the components is irrelevant to the macro fluid state and the chemical properties of the mixed fluid, and can carry out the measurement of the water content and the gas content on the complex crude oil, thereby being deeply welcomed by the oil fields.

The invention patent of CN86105543A discloses a measurement principle of utilizing single-energy γ-rays emitted by a radioactive source (such as $^{109}$Cd or $^{243}$Am and the like) to measure the volumetric water content of a two-phase oil-water mixture. The utility model patent of CN2359692Y discloses a device utilizing a $^{238}$Pu radioactive source to measure the water content in a two-phase oil-water mixture. The invention patent of CN1086602A discloses an automatic measurement instrument for measuring gas content and water content in crude oil in a three-phase oil-water-gas mixture; a γ-ray source and a transmission detector are respectively fixedly arranged in symmetrical positions on two sides on the side wall of a measurement pipeline along the radial central line; a scattering detector is fixedly arranged on the side wall of the central line which forms an included angle with the central line where the γ-ray source and the transmission detector are positioned and is apart from the central line with a certain distance along the axial direction of the measurement pipeline; and finally, the volumetric gas content and the volumetric water content are obtained by data processing based on the measured result. The utility model patent of CN2383068Y improves the device designed according to the principle, adds a stirring device and leads oil-water-gas which is actually exploited from an oil well to be mixed uniformly, thereby further meeting the theoretical assumed conditions and facilitating the improvement of the measurement precision. However, the theoretical model takes too many similar places, the physical meanings of the various parameters are not clear, and the influences on the change of pressure, temperature and the like is free from the consideration of the amendment, thereby finally affecting the using method and the measurement precision.

In addition, the γ-ray measurement method produced by using the radioactive source further has a large weakness, that is the radioactivity safety problem, and the weakness is more prominent during the current period with relatively stringent anti-terrorism situation.

For the measurement of the sand content, GB2429288A publishes a patent adopting the acoustic method to measure the sand content. That is the sand content in the fluid is estimated through the collision between the sand and the wall of an oil transportation or gas transportation pipeline. A device utilizing the design of the patent has the advantages of simple structure, convenient installation, small power consumption, long time for locally stored data and the like. But the working frequency band of the principle is the audio frequency, the interference sources are more and more complicated, the measurement result is easy to be affected by the flowing property of the fluid, and the uncertainty of the measurement is greater, thereby being incapable of meeting the needs of high-precision measurement.

At present, the methods and the devices applying the dual-energy x-ray method to measure the water content, the oil content, the gas content and the sand content during the production of the crude oil and the natural gas have not been found on the market.

Invention Contents

The invention aims at providing a method adopting the dual-energy technology to measure the gas content, the oil content, the water content or the sand content (which can only measure three indexes which are related with the corresponding mixed fluid in the four indexes) based on the demand on the real-time high-precision measurement of the water content, the oil content, the gas content or the sand content in crude oil or natural gas in an oil-water-gas or oil-water-sand or water-gas-sand three-phase mixture.

The invention provides a dual-energy x-ray measurement method of component content in the three-phase mixture which is the combination of any three of oil, water, gas and sand contained in the crude oil or the natural gas, and the measurement method comprises the following steps:

(1) Using an x-ray machine to produce single-energy or dual-energy x-rays;
(2) Leading the emitted x-rays to pass through the three-phase mixture;
(3) Using a detector sub-system to detect high-energy and low-energy data after the dual-energy x-rays pass through the three-phase mixture; or adopting the energy spectrum pre-hardening technology on a detector passage which is used as a high-energy ray detection passage to obtain high-energy data and using another detector passage as a low-energy ray detection passage to obtain low-energy data after the single-energy x-rays pass through the three-phase mixture.
(4) Solving the content of the corresponding three components in the three-phase mixture according to the following algorithm based on the measured high-energy and low-energy data;

The algorithm is as follows:

$\omega_1$, $\omega_2$ and $\omega_3$ respectively correspond to the mass percents of the three components in the mixture, from the physical meaning, we can know that $$\omega_2 = 1 - \omega_1 - \omega_3$$

$\omega_1$ and $\omega_3$ can be solved by the following two equations based on the actually measured data:

$$\left(\omega_1\left(\frac{\mu_1(E_H^*)}{\rho_1} - \frac{\mu_2(E_H^*)}{\rho_2}\right) + \omega_3\left(\frac{\mu_3(E_H^*)}{\rho_3} - \frac{\mu_2(E_H^*)}{\rho_2}\right) + \frac{\mu_2(E_H^*)}{\rho_2}\right) \cdot (x\rho) = \ln\left(\frac{k_H N_0(E_H^*)}{N(x, E_H^*) - k_H c_H N_0(E_H^*)}\right) \quad (13)$$

$$\left(\omega_1\left(\frac{\mu_1(E_L^*)}{\rho_1} - \frac{\mu_2(E_L^*)}{\rho_2}\right) + \omega_3\left(\frac{\mu_3(E_L^*)}{\rho_3} - \frac{\mu_2(E_L^*)}{\rho_2}\right) + \frac{\mu_2(E_L^*)}{\rho_2}\right) \cdot (x\rho) = \ln\left(\frac{k_L N_0(E_L^*)}{N(x, E_L^*) - k_L c_L N_0(E_L^*)}\right) \quad (14)$$

In the equations, $E_H^*$ and $E_L^*$ respectively represent equivalent energy which corresponds to the high-energy and low-energy x-rays of the x-ray machine; $\rho$ represents the actual density of the three-phase mixture, $\rho_1$ represents the density of the pure component 1 under the conditions of the corresponding temperature, the pressure and the like in an actual pipe, $\rho_2$ represents the density of the pure component 2 under the conditions of the corresponding temperature, the pressure and the like in the actual pipe, and $\rho_3$ represents the density of the pure component 3 under the conditions of the corresponding temperature, the pressure and the like in the actual pipe; $\mu_1$, $\mu_2$ and $\mu_3$ respectively represent the linear attenuation coefficients of the pure component 1, the pure component 2 and the pure component 3 under the corresponding equivalent ray energy; x represents the linear thickness of measurement space of a measurement system; $N_0(E^*)$ represents the count measured by the measurement system without the existence of any component under the condition of the corresponding equivalent ray energy $E^*$; $N(x, E^*)$ represents the count measured by the measurement system under the conditions of the corresponding measurement thickness x and the equivalent ray energy $E^*$; $E^*$ is $E_H^*$ or $E_L^*$; and k and c are correction coefficients respectively and solved by pre-measurement of an exponential decay curve together with $\mu_1$, $\mu_2$ and $\mu_3$.

Further, when the three-phase mixture is an oil-water-gas three-phase mixture in the crude oil or the natural gas, the specific meanings of $\omega_1$, $\omega_2$ and $\omega_3$ are as follows:
$\omega_1$—water content,
$\omega_2$—oil content,
$\omega_3$—gas content;

The water content, the oil content and the gas content can be solved according to the method of claim 1.

Further, when the three-phase mixture is an oil-water-sand three-phase mixture in the crude oil, the specific meanings of $\omega_1$, $\omega_2$ and $\omega_3$ are as follows:
$\omega_1$—water content,
$\omega_2$—oil content,
$\omega_3$—sand content;
The water content, the oil content and the sand content can be solved according to the method of claim 1.

Further, when the three-phase mixture is a gas-water-sand three-phase mixture in the natural gas, the specific meanings of $\omega_1$, $\omega_2$ and $\omega_3$ are as follows:
$\omega_1$—water content,
$\omega_2$—gas content,
$\omega_3$—sand content;
The water content, the gas content and the sand content can be solved according to the method of claim 1.

Further, the range of the energy $E_H^*$ of the high-energy x-ray machine is 10 keV-1 MeV, and the low-energy $E_L^*$ meets the relation formula: $E_H^* \approx (1.5\text{-}3)\, E_L^*$ or $E_H^* = 2E_L^*$.

Further, when one of $\omega_1$, $\omega_2$ and $\omega_3$ is equal to 0, the x-ray machine of the measurement system produces single-energy x-rays, and the following formula is adopted to solve the percentage content $\omega_1$ of the component 1 and the percentage content $\omega_2$ of the component 2:

$$\omega_1 = \frac{\ln\left(\frac{kN_0}{N(x)-kcN_0}\right) - \left(\frac{\mu_2}{\rho_2}\right)x\rho}{\left(\frac{\mu_1}{\rho_1}-\frac{\mu_2}{\rho_2}\right)x\rho} \quad (9)$$

$$\omega_2 = 1 - \omega_1$$

In the formula: $\rho$ represents the actual density under the two-phase state in an oil pipe, $\rho_1$ represents the density of the pure component 1 under the conditions of the corresponding temperature, the pressure and the like in the actual oil pipe, and $\rho_2$ represents the density of the pure component 2 under the conditions of the corresponding temperature, the pressure and the like in the actual oil pipe; $\mu_1$ and $\mu_2$ respectively represent the linear attenuation coefficients of the pure component 1 and the pure component 2 under the corresponding equivalent ray energy; x represents the linear thickness of the measurement space of the measurement system; $N_0$ represents the count measured by the measurement system without the existence of any component in the pipe under the condition of the corresponding equivalent ray energy; $N(x)$ represents the count measured by the measurement system under the conditions of the corresponding measurement thickness and the equivalent ray energy; and k and c are correction coefficients respectively and can be solved by pre-measurement of an exponential decay curve together with $\mu_1$ and $\mu_2$.

In order to simplify the writing process, unless otherwise specified, the following discussion only considers the coexistence situation of the oil-water-gas three-phase mixture; as for other three coexistence cases, the treatment skills are similar, only the relevant physical quantities in the description formula need to be replaced, so that the description process of other situations is omitted.

The dual-energy x-ray measurement method of the gas content and the water content in the crude oil utilizes the action principle of x-rays produced by the x-ray machine with the components to measure the indexes of the water content and the gas content in an oil transportation pipeline under the condition of coexistence of oil-water-gas three-phase media in the production of an oil field. The measurement method relies on measurement equipment consisting of three major sub-systems and a set of special software, that is a production sub-system of dual-energy x-rays, a detector sub-system composed of one or two sets of detectors and a main controlling and data processing sub-system; other devices further comprise a collimator; the detector sub-system comprises the detectors, a preamplifier or a photomultiplier tube and units for signal shaping, amplification, sampling and holding, AD conversion and the like; the main controlling and data processing sub-system comprises the parts for data transmission, synchronization, display, control, alarm and the like; the used special software adopts a special algorithm to solve the water content $\omega_1$ and the gas content $\omega_3$; $\omega_1$ represents the weight percentage the water accounts for, that is the water content, $\omega_3$ represents the weight percentage the natural gas accounts for, that is the gas content, and $\omega_2$ represents the weight percentage the oil accounts for, and $\omega_2 = 1 - \omega_1 - \omega_3$.

The software adopts the following two equations to solve the water content $\omega_1$ and the gas content $\omega_3$ under the oil-water-gas state, $$\left(\omega_1\left(\frac{\mu_1(E_H^*)}{\rho_1}-\frac{\mu_2(E_H^*)}{\rho_2}\right)+\omega_3\left(\frac{\mu_3(E_H^*)}{\rho_3}-\frac{\mu_2(E_H^*)}{\rho_2}\right)+\frac{\mu_2(E_H^*)}{\rho_2}\right)\cdot(x\rho)= \quad (13)$$
$$\ln\left(\frac{k_H N_0(E_H^*)}{N(x,E_H^*)-k_H c_H N_0(E_H^*)}\right)$$

$$\left(\omega_1\left(\frac{\mu_1(E_L^*)}{\rho_1}-\frac{\mu_2(E_L^*)}{\rho_2}\right)+\omega_3\left(\frac{\mu_3(E_L^*)}{\rho_3}-\frac{\mu_2(E_L^*)}{\rho_2}\right)+\frac{\mu_2(E_L^*)}{\rho_2}\right)\cdot(x\rho)= \quad (14)$$
$$\ln\left(\frac{k_L N_0(E_L^*)}{N(x,E_L^*)-k_L c_L N_0(E_L^*)}\right)$$

In the equations, $E_H^*$ and $E_L^*$ respectively represent equivalent energy which corresponds to the high-energy and low-energy x-rays of the x-ray machine; $\rho$ represents the actual density under the oil-water-gas three-phase state in an oil pipe, $\rho_1$ represents the density of the pure water under the conditions of the corresponding temperature, the pressure and the like in the actual oil pipe, $\rho_2$ represents the density of the pure crude oil under the conditions of the corresponding temperature, the pressure and the like in the actual oil pipe, and $\rho_3$ represents the density of the pure natural gas under the conditions of the corresponding temperature, the pressure and the like in the actual oil pipe; $\mu_1$, $\mu_2$ and $\mu_3$ respectively represent the linear attenuation coefficients of the pure water, the pure crude oil and the pure natural gas under the corresponding equivalent ray energy; x represents the linear thickness of measurement space of the measurement system in the oil pipe; $N_0(E^*)$ represents the count measured by the measurement system without the existence of any component in the oil pipe under the condition of the corresponding equivalent ray energy; $N_0(x, E^*)$ represents the count measured by the measurement system under the conditions of the corresponding measurement thickness and the equivalent ray energy; $E^*$ here refers to $E_H^*$ or $E_L^*$; and k and c are correction coefficients respectively and can be solved by pre-measurement of an exponential decay curve together with $\mu_1$, $\mu_2$ and $\mu_3$.

When only the oil-water two-phase state is considered, the energy of the x-ray machine of the measurement system can be simplified into the single-energy, and then the software adopts the following formula to solve the water content $\omega_1$, $$\omega_1 = \frac{\ln\left(\frac{kN_0}{N(x)-kcN_0}\right) - \left(\frac{\mu_2}{\rho_2}\right)x\rho}{\left(\frac{\mu_1}{\rho_1} - \frac{\mu_2}{\rho_2}\right)x\rho} \quad (9)$$

In the formula: $\rho$ represents the actual density under the oil-water two-phase state in an oil pipe, $\rho_1$ represents the density of the pure water under the conditions of the corresponding temperature, the pressure and the like in the actual oil pipe, and $\rho_2$ represents the density of the pure crude oil under the conditions of the corresponding temperature, the pressure and the like in the actual oil pipe; $\mu_1$ and $\mu_2$ respectively represent the linear attenuation coefficients of the pure water and the pure crude oil under the corresponding equivalent ray energy; x represents the linear thickness of measurement space of the measurement system in the oil pipe; $N_0$ represents the count measured by the measurement system without the existence of any component in the oil pipe under the condition of the corresponding equivalent ray energy; $N_0(x)$ represents the count measured by the measurement system under the conditions of the corresponding measurement thickness and the equivalent ray energy; and k and c are correction coefficients respectively and can be solved by pre-measurement of an exponential decay curve together with $\mu_1$ and $\mu_2$.

The design of the x-ray machine system must consider certain conditions which are met between the high-energy $E_H^*$ and the low-energy $E_L^*$, the larger the difference between the high-energy and the low-energy is, the higher the measurement precision is; for example, $E_H^* \approx (1.5\text{-}3) E_L^*$, to put it simply, $E_H^* = 2E_L^*$; and the energy range of the high-energy x-ray machine is 10 keV-1 MeV.

The dual-energy x-ray measurement technology of the invention utilizes the action principle of the x-rays produced by the x-ray machine with the components to measure the indexes of the water content and the gas content in the oil transportation pipeline under the condition of the coexistence of the oil-water-gas three-phase media in the production of the oil field. The system can overcome the serious potential safety hazard caused by radioactive sources and is particularly applicable to an automatic online counting system in the production of the oil field. The precision of the theoretical model is relatively high, the physical meanings of various parameters are relatively clear, the use is simple, and the theoretical model further considers the influences of the temperature, the pressure and other factors, thereby being particularly applicable to the automatic online counting system in the production of the oil field. When the x-ray machine is utilized as the ray source, the trouble of losing the radioactive source can be avoided, the safety coefficient of radiation protection is improved, and the opportunity of acquiring dirty bomb raw materials by terrorists is fundamentally eliminated, thereby having particularly important significance to national security.

For the coexistence situation of the oil-water-gas three-phase mixture, the derivation of the detailed theoretical basis of the measurement method of the invention is as follows: for the single-energy γ-rays, the interaction with the components follows the exponential decay law, that is the formula (1) is established.

$$N(x_m) = N_0 e^{-\mu_m \cdot x_m} \quad (1)$$

wherein: $N_0$—count measured after the rays pass through the air.

$N(x_m)$—count measured after the rays pass through the components with the mass thickness of $x_m$.

$x_m$—mass thickness of the components through which the rays pass.

$\mu_m$—mass attenuation coefficient of the components through which the rays pass.

As the energy spectrum of the x-rays produced by the x-ray machine is continuous, the energy spectra produced by a plurality of types of energy x-ray machines are shown in FIG. 1. For the x-rays with the continuous energy spectrum, whether does the interaction thereof with the components still follow the exponential decay law or not? For the theoretical research on this issue, please refer to the relevant literature.

In the relevant literature, the following propositions are deduced:

In the closed interval [c, d], the estimation of error f(x) using $ke^{-\alpha x}$ for substituting $$\sum_{i=1}^{n} k_i e^{-\alpha_1 x}$$

approximately is as follows:

$$f(x) = ke^{-\alpha x} - \sum_{i=1}^{n} k_i e^{-\alpha_i x} \quad (2)$$

Here, the [c, d] is divided into m equal parts, and the points of division are as follows:

$$c = x0 < x1 < \ldots < xm-1 < xm = d$$

$$\left(\Delta x = \frac{d-c}{m}\right)$$

At the point of division $x_j$, there is $$f(x_j) = ke^{-\alpha x_j} - \sum_{i=1}^{n} k_i e^{-\alpha_i x_j} = R_j \quad (3)$$

$$j = 0, 1, 2, \ldots, m$$

Recorded as:

$$R = \max\{|R_j| \ j = 0, 1, 2, \ldots, m\}$$

$$G = \max\left\{\sum_{i=1}^{n} k_i e^{-\alpha_i x_j} \ j = 0, 1, 2, \ldots, m\right\}$$

After some deduction, the following is obtained:

$$|f(x)| \leq R + \frac{R}{4} \cdot (\alpha \Delta x)^2 + \frac{G}{2} \alpha_{max}(\alpha_{max} - \alpha_{min})(\Delta x)^2 \quad (4)$$

In the practical application of the topic, $$\sum_{i=1}^{n} k_i e^{-\alpha_i x}$$

is equivalent to the calculation fit data; f(x) is equivalent to the absolute error which corresponds to the x point; R is equivalent to the absolute value of the maximum error in all the absolute errors; G is equivalent to maximum data in the actually measured data; a is equivalent to the equivalent mass absorption coefficient $\mu_m$; $\alpha_i$ is equivalent to the mass absorption coefficient $\mu_m(E_i)$ which corresponds to the ray energy $E_i$; x is equivalent to the mass thickness $x_m$; and $\Delta x$ is equivalent to the interval $\Delta x_m$ (independent variable) for selecting experimental data. In theory, $\Delta x$ can be very small, and the $|f(x)| \leq R$ at this time. R can be obtained by designing the experiment, thereby further obtaining the error estimation of the whole function. If the obtained maximum error is acceptable, the attenuation law can be approximated with the exponential decay law.

According to the experimental data of the theoretical analysis and the relevant literature, we found that when an absorber is not very thick, the interaction with the components approximately follows the exponential decay law, if the absorber is too thick, the error is bigger. For the specific x-ray machine, the experiment shall be firstly used for testing, thereby finding out the conditions of approximately following the exponential decay law. Then, the minimum energy $E_L^*$(which corresponds to the tube high voltage $V_L$ of the low-energy x-ray machine) of the x-ray machine is determined based on the maximum thickness of the test sample. According to the experiences, we recommend to determine the value of $E_H^*$ (which corresponds to the tube high voltage $V_H$ of the high-energy x-ray machine) according to $E_H^*=2E_L^*$.

Therefore, we assume that the x-rays of the discussed x-ray machine still approximately follow the exponential decay law in the discussed thickness range of the test sample, that is the formula (I) is approximately established. In order to realize better compliance between the theoretical model and the experimental data, two fitting coefficients of k and c are especially added, as shown in the formula (5).

$$N(x_m) = kN_0 e^{-\mu_m \cdot x_m} + c \tag{5}$$

Notes:
(1) The concept of the equivalent energy E* shall be adopted in the formula (5).
(2) The theoretical values of k and c are as follows: k=1; c=0. The theoretical values can be directly introduced in the absence of experimental values.
(3) $\mu_m(E^*)$, k and c can be measured through experiments in advance.
(4) In order to facilitate the writing, the $\mu_m(E^*)$ is hereafter abbreviated as $\mu_m$.

According to the literature, if the component is the mixture, the density is $\rho$, the linear attenuation coefficient is $\mu$, the mass attenuation coefficients of the contained elements are $$\left(\frac{\mu}{\rho}\right)_1, \left(\frac{\mu}{\rho}\right)_2, \ldots,$$

and the mass attenuation coefficient of the mixture is calculated by using the following formula:

$$\frac{\mu}{\rho} = \sum_i \left(\frac{\mu}{\rho}\right)_i \omega_i \tag{6}$$

In the formula, $\omega_1, \omega_2, \ldots, \omega_i, \ldots, \omega_N$ are mass percents of the constituent element respectively.
Note: the mass attenuation coefficient of the element is represented as $u_m$, the linear thickness is x, and the mass thickness is $x_m$. That is:

$$\mu_m = \mu/\rho \quad x_m = x \cdot \rho$$

1. The oil-water two-phase state is considered (that is, the situation that the gas phase content is 0. At this time, no subscript—crude oil-water mixed state, subscript 1—pure water state, and subscript 2—pure crude oil state)

$$\mu_m = \alpha_1 \mu_{m1} + \alpha_2 \mu_{m2} \tag{7}$$
$$= \omega_1 \mu_{m1} + (1 - \omega_1) \mu_{m2}$$
$$= \omega_1 (\mu_{m1} - \mu_{m2}) + \mu_{m2}$$

$$\because \mu_m = \frac{\mu}{\rho} \tag{8}$$

$$x_m = x \cdot \rho$$

$$\therefore \mu \cdot x = \mu_m \cdot x_m$$
$$= (\omega_1(\mu_{m1} - \mu_{m2}) + \mu_{m2}) \cdot x_m$$
$$= \left(\omega_1 \left(\frac{\mu_1}{\rho_1} - \frac{\mu_2}{\rho_2}\right) + \frac{\mu_2}{\rho_2}\right) \cdot (x\rho)$$
$$= \left(\omega_1 \left(\mu_1 \frac{\rho}{\rho_1} - \mu_2 \frac{\rho}{\rho_2}\right) + \mu_2 \frac{\rho}{\rho_2}\right) \cdot x$$

(8) is introduced into (5) and then simplified to obtain:

$$\left(\omega_1 \left(\mu_1 \frac{\rho}{\rho_1} - \mu_2 \frac{\rho}{\rho_2}\right) + \mu_2 \frac{\rho}{\rho_2}\right) \cdot x = \ln\left(\frac{kN_0}{N(x) - kcN_0}\right)$$

That is:

$$\omega_1 = \frac{\ln\left(\frac{kN_0}{N(x) - kcN_0}\right) - \left(\frac{\mu_2}{\rho_2}\right) x\rho}{\left(\frac{\mu_1}{\rho_1} - \frac{\mu_2}{\rho_2}\right) x\rho} \tag{9}$$

Under such situation, one unknown quantity of water content $\omega_1$ and one equation are obtained, so that the adoption of one single-energy x-ray machine can solve the measurement problem. This is the adopted single-energy content measurement method under the two-phase state.

2. The oil-water-gas three-phase state is considered (No subscript—crude oil+water+gas mixed state, subscript 1—pure water state, subscript 2—pure crude oil state, and subscript 3—pure natural gas state)

$$\mu_m = \alpha_1 \mu_{m1} + \alpha_2 \mu_{m2} + \alpha_3 \mu_{m3} \tag{10}$$
$$= \omega_1 \mu_{m1} + (1 - \omega_1 - \omega_3) \mu_{m2} + \omega_3 \mu_{m3}$$
$$= \omega_1(\mu_{m1} - \mu_{m2}) + \omega_3(\mu_{m3} - \mu_{m2}) + \mu_{m2}$$

$$\because \mu_m = \frac{\mu}{\rho} \tag{11}$$

$$x_m = x \cdot \rho$$

$$\therefore \mu \cdot x = \mu_m \cdot x_m$$
$$= (\omega_1(\mu_{m1} - \mu_{m2}) + \omega_3(\mu_{m3} - \mu_{m2}) + \mu_{m2}) \cdot x_m$$
$$= \left(\omega_1 \left(\frac{\mu_1}{\rho_1} - \frac{\mu_2}{\rho_2}\right) + \omega_3 \left(\frac{\mu_3}{\rho_3} - \frac{\mu_2}{\rho_2}\right) + \frac{\mu_2}{\rho_2}\right) \cdot (x\rho)$$

(11) is introduced into (5) and then simplified to obtain:

$$\left(\omega_1 \left(\frac{\mu_1}{\rho_1} - \frac{\mu_2}{\rho_2}\right) + \omega_3 \left(\frac{\mu_3}{\rho_3} - \frac{\mu_2}{\rho_2}\right) + \frac{\mu_2}{\rho_2}\right) \cdot (x\rho) = \ln\left(\frac{kN_0}{N(x) - kcN_0}\right) \tag{12}$$

In order to solve the water content $\omega_1$ and the gas content $\omega_3$, the two equations which are similar to (12) need to be listed. From the aspect of nuclear physics, the water content $\omega_1$ and the gas content $\omega_3$ can be measured through the x-rays of two x-ray machines with different energies.

Herein, the discussion adopting the dual-energy measurement model is as follows:

Assume that $E_H^*$ and $E_L^*$ respectively represent the equivalent energies which correspond to high-energy and low-energy x-rays of the x-ray machine, and then (12) can be represented as:

$$\left(\omega_1\left(\frac{\mu_1(E_H^*)}{\rho_1} - \frac{\mu_2(E_H^*)}{\rho_2}\right) + \omega_3\left(\frac{\mu_3(E_H^*)}{\rho_3} - \frac{\mu_2(E_H^*)}{\rho_2}\right) + \frac{\mu_2(E_H^*)}{\rho_2}\right) \cdot (x\rho) = \ln\left(\frac{k_H N_0(E_H^*)}{N(x, E_H^*) - k_H c_H N_0(E_H^*)}\right) \quad (13)$$

$$\left(\omega_1\left(\frac{\mu_1(E_L^*)}{\rho_1} - \frac{\mu_2(E_L^*)}{\rho_2}\right) + \omega_3\left(\frac{\mu_3(E_L^*)}{\rho_3} - \frac{\mu_2(E_L^*)}{\rho_2}\right) + \frac{\mu_2(E_L^*)}{\rho_2}\right) \cdot (x\rho) = \ln\left(\frac{k_L N_0(E_L^*)}{N(x, E_L^*) - k_L c_L N_0(E_L^*)}\right) \quad (14)$$

Theoretically, $\omega_1$ and $\omega_3$ can be solved according to the equations of (13) and (14), this is the method for measuring the water content and the gas content by using dual-energy x-rays under the oil-water-gas three-phase state, which namely is the special algorithm adopted in the invention.

Notes:
1) When $\rho_1$, $\rho_2$, $\rho_3$ and $\rho$ are measured by experiments, the influences of the temperature, the pressure and other parameters of the sample need to be simultaneously tested.
2) As the gas state is closely related with the temperature and the pressure, $\rho_3$ and $\mu_{m3}$ which are consistent with the actual conditions need to be measured during the application.
3) When the equations are solved, the look-up table method needs to be utilized, and the $\rho$ value which corresponds to the actual conditions can be obtained through real-time measurement.
4) The larger the difference between the high-energy $E_H^*$ and the low-energy $E_L^*$ is, the higher the measurement precision is. For example, $E_H^* \approx (1.5-3) E_L^*$, to put it simply, $E_H^* = 2E_L^*$.
5) Various coefficients in the formula, such as $\mu_1$, $\mu_2$, $\mu_3$, k, c and the like can be solved by respectively using the high-energy and the low-energy x-ray machines to radiate calibration media (pure crude oil, pure water and pure natural gas) with different mass thicknesses in a laboratory, and then using the least square method to fit the experimental data obtained by the attenuation measurement method. Note: k and c can be approximated by using the value which corresponds to the crude oil, the data can be also measured in the laboratory based on various situations, a database is established, and the data can be obtained by using the look-up table method during the field use. The indexes of the water content, the gas content and the like in the crude oil are finally calculated according to the deduced model of the invention (other appropriate models can also be adopted).

Further description is made below to the invention with reference to the drawings and the embodiments.

The invention further provides a measurement system of the measurement method, which consists of the following sub-systems: a production sub-system of single-energy or dual-energy (spectra) x-rays, a detector sub-system composed of one or two sets of detectors, a controlling and data processing sub-system and an additional system for calibration of long-term stability of a beam flow of an x-ray machine.

Further, the production sub-system of the dual-energy x-rays uses the x-ray machine to directly produce the x-rays with two energy spectra, the high-energy and low-energy x-rays adopt the alternate way for time division output, the x-ray machine is a true dual-energy x-ray machine sub-system, a first-line controlling unit (26) transmits high-energy and low-energy identification signals transmitted from the true dual-energy x-ray machine sub-system to a data processing computer (28), and the data processing computer (28) distinguishes the high-energy and low-energy data measured by the detectors (4) according to the identification signals.

Further, the production sub-system of the dual-energy x-rays uses two single-energy x-ray machines to produce the high-energy and low-energy x-rays, and the first group of the detectors (4) and the second group of the detectors (8) are used for measuring the high-energy and low-energy data.

Further, the production sub-system of the dual-energy x-rays uses one single-energy x-ray machine to produce the high-energy and low-energy x-rays in a time division manner through a time division prehardening device, the x-ray machine is a pseudo dual-energy x-ray machine sub-system, the first-line controlling unit (26) transmits high-energy and low-energy identification signals transmitted from the pseudo dual-energy x-ray machine sub-system to the data processing computer (28), and the data processing computer (28) distinguishes the high-energy and low-energy data measured by the detectors (4) according to the identification signals.

Further, the production sub-system of the dual-energy x-rays uses two single-energy x-ray machines which are installed in different positions to produce the high-energy and low-energy x-rays; the installation of the core parts of measurement equipment (1) adopts the transverse installation way of the two single-energy x-ray machines and the detectors, and two corresponding sets of detection passages are positioned on the same cross section of a crude oil pipeline (10) for reducing the length of the measurement equipment (1); and the range of the included angle θ between the two sets of the detection passages is as follows: 0°<θ<180°.

Further, the single-energy x-rays are produced by one x-ray machine, the x-rays with two energy spectra are realized by the detector sub-system consisting of two sets of the detectors, the high-energy x-rays are obtained by carrying out prehardening on one line of detectors, the low-energy x-rays are measured by the other line of the detectors, the measurement system is the pseudo dual-energy detector measurement system, and the data processing computer (28) carries out processing according to the high-energy and low-energy data measured by the first group of the detectors (4) and the second group of the detectors (8) of the pseudo dual-energy detector group.

Further, the x-rays with two energy spectra are realized by the detector sub-system consisting of two sets of the detectors, and two lines of the detectors applying the prehardening technology to detect the high-energy and low-energy x-rays are made into a whole pseudo dual-energy detector. The data processing computer (28) carries out processing according to a model algorithm provided in claim 1 based on the high-energy and low-energy data measured by the pseudo dual-energy detector.

Further, the additional system for the calibration of the long-term stability of the beam flow of the x-ray machine is provided with a brightness correction detector I (33) or a detector II (38) at an outlet of each x-ray machine; the brightness correction detector is in the position of the outlet of the x-ray machine and deviates from a main beam flow for measurement, and the real-time calibration is carried out on the dose change of the x-ray machine based on the data measured by the brightness correction detector I (33) or the detector II (38), thereby eliminating the measurement error caused by the dose change of the x-ray machine.

BRIEF DESCRIPTION OF THE DRAWINGS

FIG. 1-1 is an energy spectrum chart of 20 keV molybdenum target x-ray machine;

FIG. 1-2 is an energy spectrum chart of 30 keV molybdenum target x-ray machine;

FIG. 1-3 is an energy spectrum chart of 35 keV molybdenum target x-ray machine;

FIG. 1-4 is an energy spectrum chart of 50 keV molybdenum target x-ray machine;

FIG. 2 is a schematic diagram of installation way of true dual-energy x-ray machine and detectors;

FIG. 3 is a schematic diagram of longitudinal installation way of two single-energy x-ray machines and detectors;

FIG. 4 is a schematic diagram of installation way of pseudo dual-energy x-ray machine and detectors;

Figure 2:
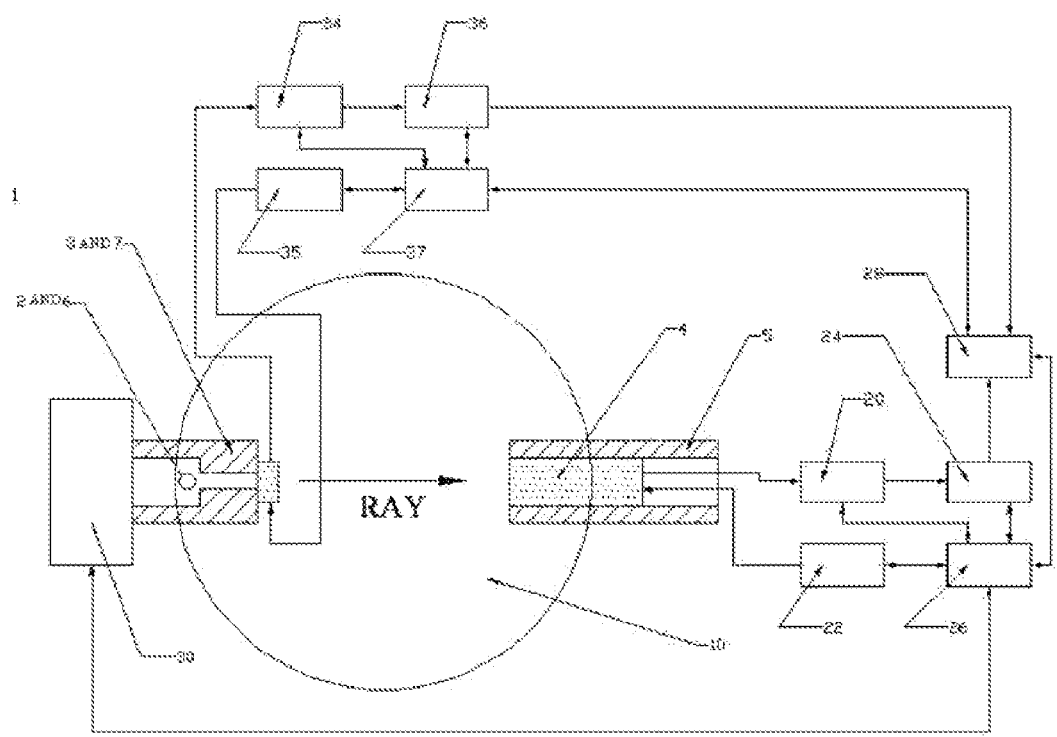

Meanings of symbols in the drawings are as follows: 1—measurement equipment; 2—target point of high-energy x-ray machine; 3—collimator and shielding room of high-energy x-ray machine; 4—(first group of) detectors; 5—shielding tube of (first group of) detectors; 6—target point of low-energy x-ray machine; 7—collimator and shielding room of low-energy x-ray machine; 8—second group of detectors; 9—shielding tube of second group of detectors; 10—crude oil pipeline; 12—energy spectrum prehardening device; 13—rotating mechanism; 20—(first-line) signal shaping, amplifying and sample-holding unit; 21—second-line signal shaping, amplifying and sample-holding unit; 22—high-voltage power supply of (first group of) detectors; 23—high-voltage power supply of second group of detectors; 24—(first-line) AD conversion unit; 25—second-line AD conversion unit; 26—(first-line) controlling unit; 27—second-line controlling unit; 28—computer; 30—controlling system of true dual-energy x-ray machine; 31—controlling system of high-energy x-ray machine; 32—controlling system of low-energy x-ray machine; 33—(first-line) brightness correction detector; 34—third-line signal shaping, amplifying and sample-holding unit; 35—high-voltage power supply of third-line detector; 36—third-line AD conversion unit; 37—third-line controlling unit; 38—second-line brightness correction detector; 39—fourth-line signal shaping, amplifying and sample-holding unit; 40—high-voltage power supply of fourth-line detector; 41—fourth-line AD conversion unit; 42—fourth-line controlling unit; and 50—energy spectrum filter disc.

DETAILED DESCRIPTION

According to the measurement method of the invention, the application examples of the following five measurement systems are given:

1. Working Principle of True Dual-Energy X-Ray Machine Measurement System

The installation positions of the core parts of the measurement equipment 1 are as shown in FIG. 2.

The true dual-energy x-ray machine is characterized in that the positions of the target point 2 of the high-energy x-rays and the target point 6 of the low-energy x-rays are basically superposed, the controlling system 30 of the true dual-energy x-ray machine controls the time division alternate output of the high-energy and low-energy x-rays, and the frequency of output pulses is related to the velocity of the fluid. Theoretically, it is expected that the high-energy and low-energy x-rays can simultaneously hit the same position on the medium; in practice, the parameters can be regulated according to the uniformity, the flow rate, the required interval for monitoring the data and the like of the medium, thereby ensuring that the test conditions can meet the theoretical model and the error requirements as far as possible.

The x-rays emitted from the target points 2 and 6 pass through the collimators 3 and 7 (the two have been combined into a whole, and two symbols are specially retained for being consistent with the serial numbers in other examples in the following text), then pass through the medium in the crude oil pipeline 10, and are converted into electrical signals by the detectors 4. The roles of the shielding tube 5 of the detectors are to protect the detectors 4 and reduce the impacts on the detectors caused by detection background and scattering signals.

The high-voltage power supply 22 of the detectors provides the working voltage for the detectors 4, the signals of the detectors 4 are outputted to the signal shaping, amplifying and sample-holding unit 20, the signals are sent to the AD conversion unit 24 and converted to digital signals after amplification and treatment, and the signals are finally sent to the computer 28 for analysis and treatment. The controlling unit 26 is used for synchronizing and coordinating the work of all the units or the sub-systems.

In the example, the second set of the detector system is omitted, and the identification and the synchronization of the high-energy and low-energy signals are realized through the signal interaction of the controlling system 30 of the true dual-energy x-ray machine and the controlling unit 26.

If the beam flow of the x-ray machine changes greatly along with the time, the beam flow is unstable, and the beam flow needs to be corrected during the actual data treatment. In order to obtain the variable quantity of the beam flow of the x-ray machine along with the time, a detection system for brightness correction needs to be added. That is: a line of brightness correction detector 33 is mounted at the outlet of the x-ray machine, the high-voltage power supply 35 of the third-line detector provides the high voltage for the detector 33, the signal of the detector 33 is outputted to the third-line signal shaping, amplifying and sample-holding unit 34, the signal is sent to the third-line AD conversion unit 36 and converted to the digital signal after amplification and treatment, and the signal is finally sent to the computer 28 for analysis and treatment. The controlling unit 37 is used for synchronizing and coordinating the work of all the units or the sub-systems.

If the beam flow of the x-ray machine is stable, the error caused by the measurement of the system can be ignored, and the detection system about the brightness correction can be omitted.

The special software on the computer 28 firstly respectively amends all the data at the corresponding time, including the high-energy group data series and the low-energy group data series which are formed by dividing the detected data, and the high-energy and low-energy data obtained by applying the brightness detector. The influences caused by the change of the beam flow of the x-ray machine along with the time are firstly eliminated. Then, the indexes of the water content, the gas content and the like in the crude oil are calculated by applying the model deduced in the invention (other appropriate models can also be adopted).

Figure 3:
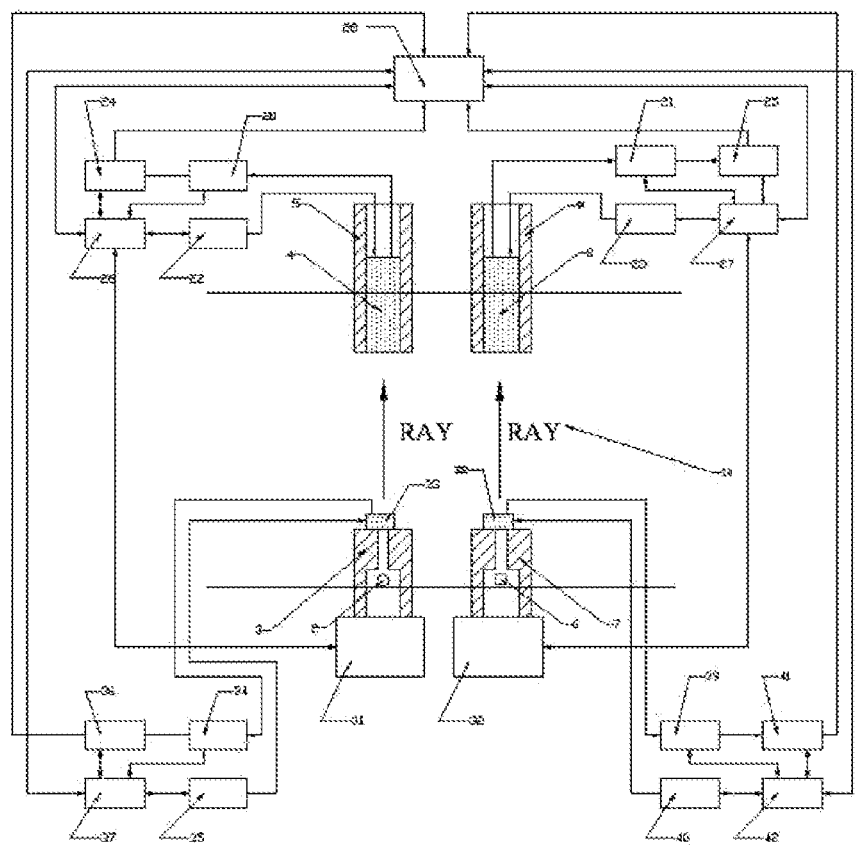

2. Working Principle of Measurement System with Longitudinal Installation Way of Two Single-Energy X-Ray Machines and Detectors The installation positions of the core parts of the measurement equipment 1 are as shown in FIG. 3.

The application example is characterized by utilizing the existing two single-energy x-ray machines to produce the high-energy and low-energy x-rays. The target point 2 of the high-energy x-rays, the collimator 3, the detectors 4, the shielding tube 5 and the like constitute a set of high-energy x-ray detection passage, and the target point 6 of the low-energy x-rays, the collimator 7, the detectors 8, the shielding tube 9 and the like constitute a set of low-energy x-ray detection passage in a similar way. The closer the two sets of the detection passages get, the better the ideal requirement that the high-energy and low-energy x-rays simultaneously hit the same position of the medium theoretically is met. In practice, the parameters can be regulated according to the uniformity, the flow rate, the required interval for monitoring the data and the like of the medium, thereby ensuring that the test conditions can meet the theoretical model and the error requirements as far as possible.

The controlling system 31 of the high-energy x-ray machine controls the target point 2 of the high-energy x-ray machine to emit the high-energy x-rays, and the x-rays pass through the collimator and the shielding room 3, then pass through the medium in the crude oil pipeline 10 and are further converted to the electrical signals by the first group of the detectors 4. The roles of the shielding tube 5 of the first group of the detectors are to protect the first group of the detectors 4 and simultaneously reduce the impacts on the first group of the detectors caused by background and scattering signals. The high-voltage power supply 22 of the first group of the detectors provides the working voltage for the first group of the detectors 4, the signals of the first group of the detectors 4 are outputted to the first-line signal shaping, amplifying and sample-holding unit 20, the signals are sent to the first-line AD conversion unit 24 and converted to the digital signals after amplification and treatment, and the signals are finally sent to the computer 28 for analysis and treatment. The first-line controlling unit 26 is used for synchronizing and coordinating the work of all the units or the relevant sub-systems.

In the similar way, the controlling system 32 of the low-energy x-ray machine controls the target point 6 of the low-energy x-ray machine to emit the low-energy x-rays, and the x-rays pass through the collimator and the shielding room 7, then pass through the medium in the crude oil pipeline 10 and are further converted to the electrical signals by the second group of the detectors 8. The roles of the shielding tube 9 of the second group of the detectors are to protect the second group of the detectors 8 and simultaneously reduce the impacts on the second group of the detectors caused by the background and the scattering signals. The high-voltage power supply 23 of the second group of the detectors provides the working voltage for the second group of the detectors 8, the signals of the second group of the detectors 8 are outputted to the second-line signal shaping, amplifying and sample-holding unit 21, the signals are sent to the second-line AD conversion unit 25 and converted to the digital signals after amplification and treatment, and the signals are finally sent to the computer 28 for analysis and treatment. The second-line controlling unit 27 is used for synchronizing and coordinating the work of all the units or the relevant sub-systems.

In the example, the design requirements on the x-ray machine are reduced, and the example only needs to use products in the market. The high and low signals in the same position can be synchronized by using the velocity and the detection time of the fluid.

If the beam flow of the x-ray machine changes greatly along with the time, the beam flow needs to be corrected during the actual data treatment. In order to obtain the variable quantity of the beam flow of the x-ray machine along with the time, the detection system for brightness correction needs to be added. That is: the first-line brightness correction detector 33 is mounted at the outlet of the high-energy x-ray machine, the high-voltage power supply 35 of the third-line detector provides the high voltage for the detector 33, the signal of the detector 33 is outputted to the third-line signal shaping, amplifying and sample-holding unit 34, the signal is sent to the third-line AD conversion unit 36 and converted to the digital signal after amplification and treatment, and the signal is finally sent to the computer 28 for analysis and treatment. The controlling unit 37 is used for synchronizing and coordinating the work of all the units or the sub-systems.

In the similar way, in order to obtain the variable quantity of the beam flow of the low-energy x-ray machine along with the time, the second-line brightness correction detector 38 is mounted at the outlet of the low-energy x-ray machine, the high-voltage power supply 40 of the fourth-line detector provides the high voltage for the detector 38, the signal of the detector 38 is outputted to the fourth-line signal shaping, amplification, sampling and holding unit 39, the signal is sent to the fourth-line AD conversion unit 41 and converted to the digital signal after amplification and treatment, and the signal is finally sent to the computer 28 for analysis and treatment. The fourth-line controlling unit 42 is used for synchronizing and coordinating the work of all the units or the sub-systems.

If the beam flow of the x-ray machine is stable, the error caused by the measurement of the system can be ignored, and the detection system about the brightness correction can be omitted.

The special software on the computer 28 firstly respectively amends all the data at the corresponding time, including the high-energy group data and the low-energy group data obtained by detection and the high-energy and low-energy data obtained by applying the brightness detector. The influences caused by the change of the beam flow of the x-ray machine along with the time are firstly eliminated. Then, the indexes of the water content, the gas content and the like in the crude oil are calculated by applying the model deduced in the invention (other appropriate models can also be adopted).

3. Working Principle of Pseudo Dual-Energy X-Ray Machine Measurement System

Figure 4:
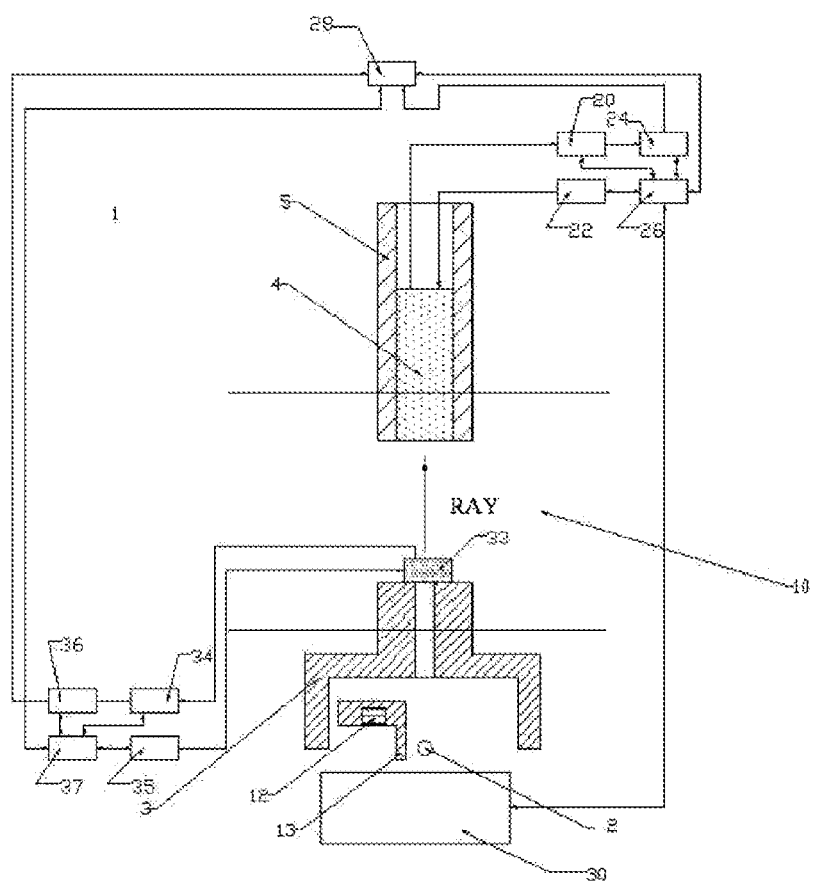

The installation positions of the core parts of the measurement equipment 1 are as shown in FIG. 4.

The application example is characterized by utilizing the existing one single-energy x-ray machine to produce the high-energy and low-energy x-rays through the time division prehardening technology. The target point 2 of the x-ray machine, the collimator 3, the detectors 4 and the shielding tube 5 constitute a set of x-ray detection passage. An energy spectrum prehardening device 12 and a rotating mechanism 13 are mounted together, and the rotation center of the rotating mechanism 13 can not block the target point 2 of the x-ray machine. When the rotation position of the rotating mechanism 13 can lead the energy spectrum prehardening device 12 to block the x-rays emitted by the target point 2, the x-rays emitted from the collimator 3 are the high-energy x-rays, and the system can be used as the high-energy measurement system. Otherwise, the system can be used as the low-energy measurement system. In practice, the rotation velocity of the rotating mechanism 13 can be regulated according to the uniformity, the flow rate, the required interval for monitoring the data and the like of the medium, thereby ensuring that the test conditions can meet the theoretical model and the error requirements as far as possible.

The x-rays emitted from the target point 2 pass through the collimator 3, then pass through the medium in the crude oil pipeline 10 and are converted to the electrical signals by the detectors 4. The roles of the shielding tube 5 of the detectors are to protect the detectors 4 and simultaneously reduce the impacts on the detectors caused by detection background and scattering signals. The high-voltage power supply 22 of the detectors provides the working voltage for the detectors 4, the signals of the detectors 4 are outputted to the signal shaping, amplifying and sample-holding unit 20, the signals are sent to the AD conversion unit 24 and converted to digital signals after amplification and treatment, and the signals are finally sent to the computer 28 for analysis and treatment. The controlling unit 26 is used for synchronizing and coordinating the work of all the units or the sub-systems. Particularly, the identification of the high-energy and low-energy is realized through the signal interaction of the controlling system 30 of the x-ray machine and the controlling unit 26.

In the example, the design requirements on the x-ray machine are reduced, and the example only needs to use products in the market.

If the beam flow of the x-ray machine changes greatly along with the time, the beam flow needs to be corrected during the actual data treatment. In order to obtain the variable quantity of the beam flow of the x-ray machine along with the time, a detection system for brightness correction needs to be added. That is: a line of brightness correction detector 33 is mounted at the outlet of the x-ray machine, the high-voltage power supply 35 of the third-line detector provides the high voltage for the detector 33, the signal of the detector 33 is outputted to the third-line signal shaping, amplifying and sample-holding unit 34, the signal is sent to the third-line AD conversion unit 36 and converted to the digital signal after amplification and treatment, and the signal is finally sent to the computer 28 for analysis and treatment. The controlling unit 37 is used for synchronizing and coordinating the work of all the units or the sub-systems.

If the beam flow of the x-ray machine is stable, the error caused by the measurement of the system can be omitted, and the detection system about the brightness correction can be omitted.

The special software on the computer 28 firstly respectively amends all the data at the corresponding time, including the high-energy group data series and the low-energy group data series formed by dividing the detected data and the high-energy and low-energy data obtained by applying the brightness detector. The influences caused by the change of the beam flow of the x-ray machine along with the time are firstly eliminated. Then, the indexes of the water content, the gas content and the like in the crude oil are calculated by applying the model deduced in the invention (other appropriate models can also be adopted).

Figure 5:
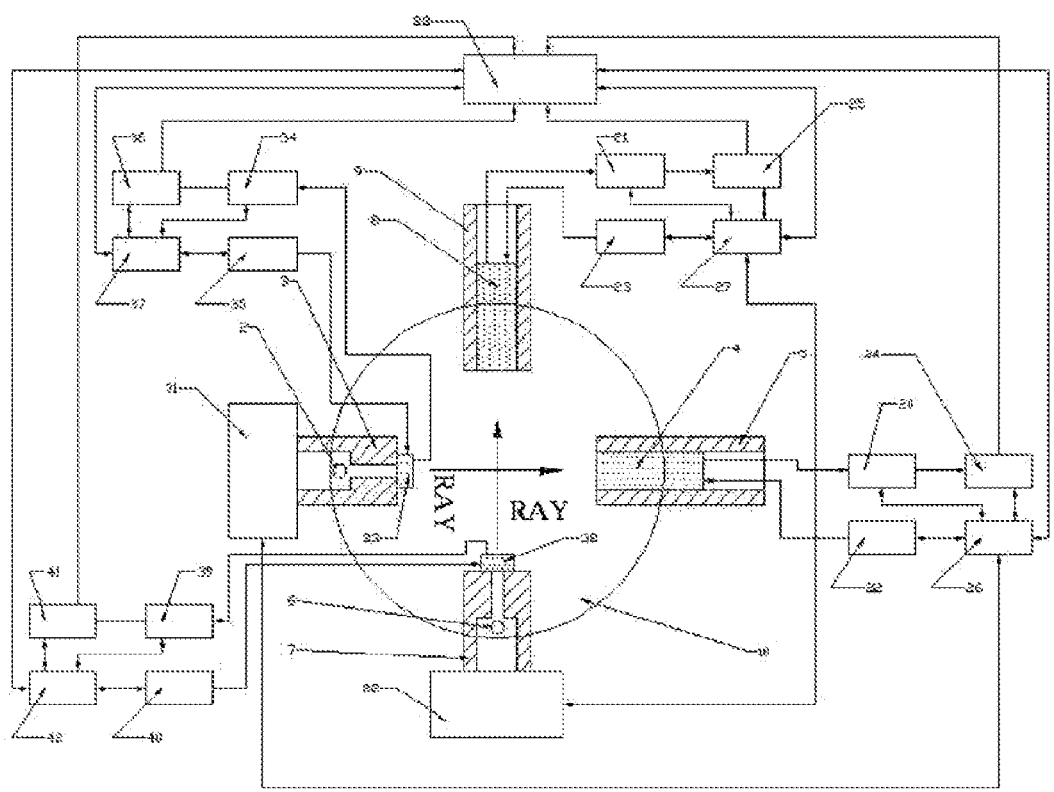
FIG. 5 is a schematic diagram of transverse installation way of two single-energy x-ray machines and detectors.

4. Working Principle of Measurement System with Transverse Installation Way of Two Single-Energy X-Ray Machines and Detectors The installation positions of the core parts of the measurement equipment 1 are as shown in FIG. 5.

The application example is characterized by utilizing the existing two single-energy x-ray machines to produce the high-energy and low-energy x-rays. The target point 2 of the high-energy x-ray machine, the collimator 3, the detectors 4 and the shielding tube 5 constitute a set of high-energy x-ray detection passage, and the target point 6 of the low-energy x-ray machine, the collimator 7, the detectors 8 and the shielding tube 9 constitute a set of low-energy x-ray detection passage in a similar way. The two sets of the detection passages are arranged on the same cross section of the crude oil pipeline 10, thereby reducing the length of the measurement equipment 1. Note: as long as the test parts can be completely mounted well, the included angle between the two sets of the detection passages as shown in the FIG. 5 is not necessarily required to be 90°. The example requires that the distribution of the fluid on the same cross section of the crude oil pipeline 10 is approximately the same, thereby meeting the ideal requirement that the high-energy and low-energy x-rays simultaneously hit the same position on the medium in theory. In the practical application, measurements can be taken to stir the fluid before the medium flows into the test equipment, thereby uniformly mixing the fluid.

The controlling system 31 of the high-energy x-ray machine controls the target point 2 of the high-energy x-ray machine to emit the high-energy x-rays, and the x-rays pass through the collimator and the shielding room 3, then pass through the medium in the crude oil pipeline 10 and are further converted to the electrical signals by the first group of the detectors 4. The roles of the shielding tube 5 of the first group of the detectors are to protect the first groups of the detectors 4 and simultaneously reduce the impacts on the first group of the detectors caused by background and scattering signals. The high-voltage power supply 22 of the first group of the detectors provides the working voltage for the first group of the detectors 4, the signals of the first group of the detectors 4 are outputted to the first-line signal shaping, amplifying and sample-holding unit 20, the signals are sent to the first-line AD conversion unit 24 and converted to the digital signals after amplification and treatment, and the signals are finally sent to the computer 28 for analysis and treatment. The first-line controlling unit 26 is used for synchronizing and coordinating the work of all the units or the relevant sub-systems.

In the similar way, the controlling system 32 of the low-energy x-ray machine controls the target point 6 of the low-energy x-ray machine to emit the low-energy x-rays, and the x-rays pass through the collimator and the shielding room 7, then pass through the medium in the crude oil pipeline 10 and are further converted to the electrical signals by the second group of the detectors 8. The roles of the shielding tube 9 of the second group of the detectors are to protect the second group of the detectors 8 and simultaneously reduce the impacts on the second group of the detectors caused by the background and the scattering signals. The high-voltage power supply 23 of the second group of the detectors provides the working voltage for the second group of the detectors 8, the signals of the second group of the detectors 8 are outputted to the second-line signal shaping, amplifying and sample-holding unit 21, the signals are sent to the second-line AD conversion unit 25 and converted to the digital signals after amplification and treatment, and the signals are finally sent to the computer 28 for analysis and treatment. The second-line controlling unit 27 is used for synchronizing and coordinating the work of all the units or the relevant sub-systems.

In the example, the design requirements on the x-ray machine are reduced, and the example only needs to use products in the market. The high and low signals in the same position can adopt the measure of mixing the fluid, thereby keeping the cross section of the fluid uniform and further approximating the conditions of the theoretical model.

If the beam flow of the x-ray machine changes greatly along with the time, the beam flow needs to be corrected during the actual data treatment. In order to obtain the variable quantity of the beam flow of the x-ray machine along with the time, the detection system for brightness correction needs to be added. That is: the first-line brightness correction detector 33 is mounted at the outlet of the high-energy x-ray machine, the high-voltage power supply 35 of the third-line detector provides the high voltage for the detector 33, the signal of the detector 33 is outputted to the third-line signal shaping, amplifying and sample-holding unit 34, the signal is sent to the third-line AD conversion unit 36 and converted to the digital signal after amplification and treatment, and the signal is finally sent to the computer 28 for analysis and treatment. The controlling unit 37 is used for synchronizing and coordinating the work of all the units or the sub-systems.

In the similar way, in order to obtain the variable quantity of the beam flow of the low-energy x-ray machine along with the time, the second-line brightness correction detector 38 is mounted at the outlet of the low-energy x-ray machine, the high-voltage power supply 40 of the fourth-line detector provides the high voltage for the detector 38, the signal of the detector 38 is outputted to the fourth-line signal shaping, amplifying and sample-holding unit 39, the signal is sent to the fourth-line AD conversion unit 41 and converted to the digital signal after amplification and treatment, and the signal is finally sent to the computer 28 for analysis and treatment. The fourth-line controlling unit 42 is used for synchronizing and coordinating the work of all the units or the sub-systems.

If the beam flow of the x-ray machine is stable, the error caused by the measurement of the system can be omitted, and the detection system about the brightness correction can be omitted.

The special software on the computer 28 firstly respectively amends all the data at the corresponding time, including the high-energy group data series and the low-energy group data series obtained by detection and the high-energy and low-energy data obtained by applying the brightness detector. The influences caused by the change of the beam flow of the x-ray machine along with the time are firstly eliminated. Then, the indexes of the water content, the gas content and the like in the crude oil are calculated by applying the model deduced in the invention (other appropriate models can also be adopted).

Figure 6:
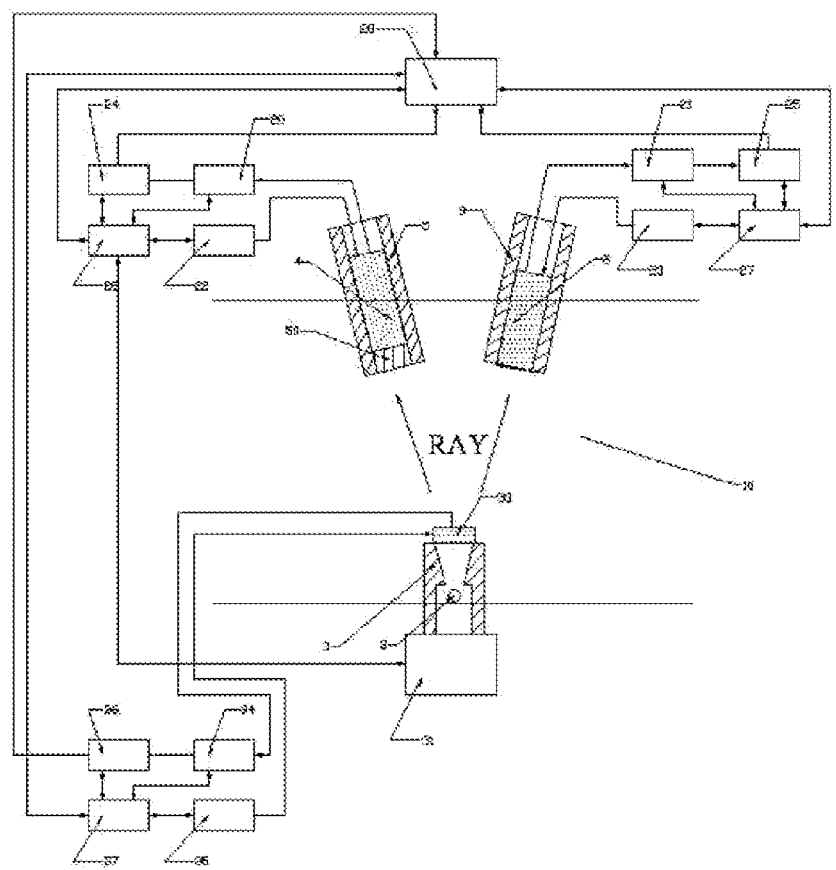
FIG. 6 is a schematic diagram of installation way of single-energy x-ray machine and pseudo dual-energy detectors (two groups of the detectors can also be arranged in other positions, such as on the same cross section)

5. Installation Way of Single-Energy X-Ray Machine and Pseudo Dual-Energy Detectors The installation positions of the core parts of the measurement equipment 1 are as shown in FIG. 6. Note: the two lines of the detectors can also be mounted in other positions, such as the same cross section of the crude oil pipeline 10.

The application example is characterized by utilizing the existing single-energy x-ray machine to produce the high-energy x-ray detection passage by adopting the prehardening technology on one line of the detector, and produce the low-energy x-ray detection passage by adopting the prehardening technology on the other line of the detector. An energy spectrum filter disc 50 is mounted in front of the detectors 4, and the target point 2 of the x-ray machine, the collimator 3, the energy spectrum filter disc 50, the detectors 4 and the shielding tube 5 constitute a set of high-energy x-ray detection passage. At this time, this line of the system is used as the high-energy measurement system. The target point 2 of the x-ray machine, the collimator 3, the second group of the detectors 8 and the shielding tube 9 of the second group of the detectors constitute the other set of low-energy x-ray detection passage, and this line of the system is used as the low-energy measurement system.

The first line: the x-rays emitted from the target point 2 pass through the collimator 3, then pass through the medium in the crude oil pipeline 10, are changed to high-energy energy spectrum after energy spectrum prehardening through the energy spectrum filter disc 50, and are further converted to electrical signals by the detectors 4. The roles of the shielding tube 5 of the detectors are to protect the detectors 4 and simultaneously reduce the impacts on the detectors 4 caused by detection background and scattering signals. The high-voltage power supply 22 of the detectors provides the working voltage for the detectors 4, the signals of the detectors 4 are outputted to the signal shaping, amplifying and sample-holding unit 20, the signals are sent to the AD conversion unit 24 and converted to digital signals after amplification and treatment, and the signals are finally sent to the computer 28 for analysis and treatment. The controlling unit 26 is used for synchronizing and coordinating the work of all the units or the sub-systems.

The second line: the x-rays emitted from the target point 2 pass through the collimator 3, then pass through the medium in the crude oil pipeline 10 and are converted to the electrical signals by the second group of the detectors 8. The roles of the shielding tube 9 of the second group of the detectors are to protect the detectors 8 and simultaneously reduce the impacts on the detectors 8 caused by the detection background and the scattering signals. The high-voltage power supply 23 of the second group of the detectors provides the working voltage for the detectors 8, the signals of the detectors 8 are outputted to the second-line signal shaping, amplifying and sample-holding unit 21, the signals are sent to the second-line AD conversion unit 25 and converted to the digital signals after amplification and treatment, and the signals are finally sent to the computer 28 for analysis and treatment. The second-line controlling unit 27 is used for synchronizing and coordinating the work of all the units or the sub-systems.

In the example, the design requirements on the x-ray machine are reduced, and the example only needs to use products in the market.

If the beam flow of the x-ray machine changes greatly along with the time, the beam flow needs to be corrected during the actual data treatment. In order to obtain the variable quantity of the beam flow of the x-ray machine along with the time, a detection system for brightness correction needs to be added. That is: a line of brightness correction detector 33 is mounted at the outlet of the x-ray machine, the high-voltage power supply 35 of the third-line detector provides the high voltage for the detector 33, the signal of the detector 33 is outputted to the third-line signal shaping, amplifying and sample-holding unit 34, the signal is sent to the third-line AD conversion unit 36 and converted to the digital signal after amplification and treatment, and the signal is finally sent to the computer 28 for analysis and treatment. The controlling unit 37 is used for synchronizing and coordinating the work of all the units or the sub-systems.

If the beam flow of the x-ray machine is stable, the error caused by the measurement of the system can be ignored, and the detection system about the brightness correction can be omitted.

The special software on the computer 28 firstly respectively amends all the data at the corresponding time, including the high-energy group data series and the low-energy group data series formed by dividing the detected data and the high-energy and low-energy data obtained by applying the brightness detector. The influences caused by the change of the beam flow of the x-ray machine along with the time are firstly eliminated. Then, the indexes of the water content, the gas content and the like in the crude oil are calculated by applying the model deduced in the invention (other appropriate models can also be adopted).

6. Another Installation Way of X-Ray Machine and Pseudo Dual-Energy Detector

Figure 7:
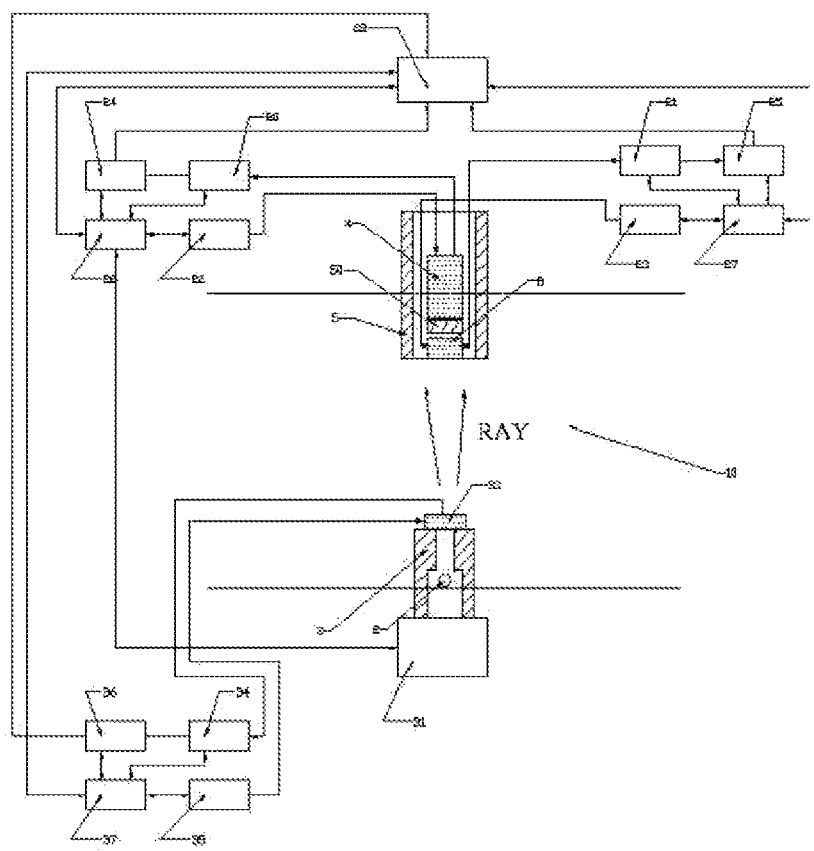
FIG. 7 is a schematic diagram of installation way of single-energy x-ray machine and integrated pseudo dual-energy detector.

Another installation way of the single-energy x-ray machine and the pseudo dual-energy detector is as shown in FIG. 7. Two lines of high and low detectors are integrated into a whole.

The embodiment is characterized by utilizing the existing single-energy x-ray machine to produce the high-energy x-ray detection passage by adopting the prehardening technology on one line of the detector, and produce the low-energy x-ray detection passage by adopting the prehardening technology on the other line of the detector. The target point 2 of the x-ray machine, the collimator 3, the second group of the detectors 8 and the shielding tube 5 of the detectors constitute a set of low-energy x-ray detection passage, and this line of the system is used as the low-energy measurement system; and the energy spectrum filter disc 50 is mounted in front of the detectors 4, but behind the second group of the detectors 8, the target point 2 of the x-ray machine, the collimator 3, the energy spectrum filter disc 50, the detectors 4 and the shielding tube 5 constitute a set of high-energy x-ray detection passage. This line of the system is used as the high-energy measurement system. Note: this line of the rays also pass through the low-energy x-ray detectors 8, and the second group of the detectors 8 and the energy spectrum filter disc 50 play the same role.

The first line: the x-rays emitted from the target point 2 pass through the collimator 3, then pass through the medium in the crude oil pipeline 10, are changed to high-energy energy spectrum after energy spectrum prehardening through the second group of the detectors 8 and the energy spectrum filter disc 50, and are further converted to electrical signals by the detectors 4. The roles of the shielding tube 5 of the detectors are to protect the detectors 4 and simultaneously reduce the impacts on the detectors 4 caused by detection background and scattering signals. The high-voltage power supply 22 of the detectors provides the working voltage for the detectors 4, the signals of the detectors 4 are outputted to the signal shaping, amplifying and sample-holding unit 20, the signals are sent to the AD conversion unit 24 and converted to digital signals after amplification and treatment, and the signals are finally sent to the computer 28 for analysis and treatment. The controlling unit 26 is used for synchronizing and coordinating the work of all the units or the sub-systems.

The second line: the x-rays emitted from the target point 2 passthrough the collimator 3, then pass through the medium in the crude oil pipeline 10 and are converted to the electrical signals by the second group of detectors 8. The roles of the shielding tube 5 of the detectors are to protect the detectors 8 and simultaneously reduce the impacts on the detectors 8 caused by the detection background and scattering signals. The high-voltage power supply 23 of the second group of the detectors provides the working voltage for the detectors 8, the signals of the detectors 8 are outputted to the second-line signal shaping, amplifying and sample-holding unit 21, the signals are sent to the second-line AD conversion unit 25 and converted to the digital signals after amplification and treatment, and the signals are finally sent to the computer 28 for analysis and treatment. The second-line controlling unit 27 is used for synchronizing and coordinating the work of all the units or the sub-systems.

In the example, the new detector manufacturing process is adopted to make new pseudo dual-energy detector, thereby reducing the design requirements on the x-ray machine, and the example only needs to use the products in the current market.

If the beam flow of the x-ray machine changes greatly along with the time, the beam flow needs to be corrected during the actual data treatment. In order to obtain the variable quantity of the beam flow of the x-ray machine along with the time, a detection system for brightness correction needs to be added. That is: a line of brightness correction detector 33 is mounted at the outlet of the x-ray machine, the high-voltage power supply 35 of the third-line detector provides the high voltage for the detector 33, the signal of the detector 33 is outputted to the third-line signal shaping, amplifying and sample-holding unit 34, the signal is sent to the third-line AD conversion unit 36 and converted to the digital signal after amplification and treatment, and the signal is finally sent to the computer 28 for analysis and treatment. The controlling unit 37 is used for synchronizing and coordinating the work of all the units or the sub-systems.

If the beam flow of the x-ray machine is stable, the error caused by the measurement of the system can be ignored, and the detection system about the brightness correction can be omitted.

The special software on the computer 28 firstly respectively amends all the data at the corresponding time, including the high-energy group data series and the low-energy group data series formed by dividing the detected data and the high-energy and low-energy data obtained by applying the brightness detector. The influences caused by the change of the beam flow of the x-ray machine along with the time are firstly eliminated. Then, the indexes of the water content, the gas content and the like in the crude oil are calculated by applying the model deduced in the utility model (other appropriate models can also be adopted).

The invention claimed is:
1. A dual-energy x-ray measurement method of constituent content in a three-phase mixture which is the combination of any three of oil, water, gas and sand contained in crude oil or natural gas, wherein the measurement method comprises the following steps:
(1) Using an x-ray machine to produce single-energy or dual-energy x-rays;
(2) Leading the emitted x-rays to pass through the three-phase mixture;
(3) Using a detector sub-system to detect high-energy and low-energy data after the dual-energy x-rays pass through the three-phase mixture; or adopting the energy spectrum prehardening technology on a detector passage which is used as a high-energy ray detection passage to obtain high-energy data and using another detector passage as a low-energy ray detection passage to obtain low-energy data after the single-energy x-rays pass through the three-phase mixture;
(4) Solving the content of the corresponding three components in the three-phase mixture according to algorithm based on the measured high-energy and low-energy data, and the algorithm is as follows:
$\omega_1$, $\omega_2$ and $\omega_3$ respectively correspond to the mass percents of the three components in the mixture, from the physical meaning, we can know that

$$\omega_2 = 1 - \omega_1 - \omega_3$$

$\omega_1$ and $\omega_3$ can be solved by the following two equations based on the actually measured data:

$$\left(\omega_1\left(\frac{\mu_1(E_H^*)}{\rho_1} - \frac{\mu_2(E_H^*)}{\rho_2}\right) + \omega_3\left(\frac{\mu_3(E_H^*)}{\rho_3} - \frac{\mu_2(E_H^*)}{\rho_2}\right) + \frac{\mu_2(E_H^*)}{\rho_2}\right) \cdot (x\rho) = \quad (13)$$

$$\ln\left(\frac{k_H N_0(E_H^*)}{N(x, E_H^*) - k_H c_H N_0(E_H^*)}\right)$$

$$\left(\omega_1\left(\frac{\mu_1(E_L^*)}{\rho_1} - \frac{\mu_2(E_L^*)}{\rho_2}\right) + \omega_3\left(\frac{\mu_3(E_L^*)}{\rho_3} - \frac{\mu_2(E_L^*)}{\rho_2}\right) + \frac{\mu_2(E_L^*)}{\rho_2}\right) \cdot (x\rho) = \quad (14)$$

$$\ln\left(\frac{k_L N_0(E_L^*)}{N(x, E_L^*) - k_L c_L N_0(E_L^*)}\right)$$

In the equations, $E_H^*$ and $E_L^*$ respectively represent equivalent energies which correspond to the high-energy and low-energy x-rays of the x-ray machine; $\rho$ represents the actual density of the three-phase mixture, $\rho_1$ represents the density of the pure component 1 under the conditions of the corresponding temperature, the pressure and the like in an actual pipe, $\rho_2$ represents the density of the pure component 2 under the conditions of the corresponding temperature, the pressure and the like in the actual pipe, and $\rho_3$ represents the density of the pure component 3 under the conditions of the corresponding temperature, the pressure and the like in the actual pipe; $\mu_1$, $\mu_2$ and $\mu_3$ respectively represent the linear attenuation coefficients of the pure component 1, the pure component 2 and the pure component 3 under the corresponding equivalent ray energy; x represents the linear thickness of measurement space of a measurement system; $N_0(E^*)$ represents the count measured by the measurement system without the existence of any component under the condition of the corresponding equivalent ray energy; $N(x, E^*)$ represents the count measured by the measurement system under the conditions of the corresponding measurement thickness x and the equivalent ray energy; $E^*$ is $E_H^*$ or $E_L^*$; and k and c are correction coefficients respectively and solved by pre-measurement of an exponential decay curve together with $\mu_1$, $\mu_2$ and $\mu_3$.

2. The dual-energy x-ray measurement method of the constituent content in the three-phase mixture of claim 1, wherein when the three-phase mixture is an oil-water-gas three-phase mixture in the crude oil or the natural gas, the specific meanings of $\omega_1$, $\omega_2$ and $\omega_3$ are as follows:
$\omega_1$—water content, $\omega_2$—oil content and $\omega_3$—gas content.

3. The dual-energy x-ray measurement method of the constituent content in the three-phase mixture of claim 1, wherein when the three-phase mixture is an oil-water-sand three-phase mixture in the crude oil, the specific meanings of $\omega_1$, $\omega_2$ and $\omega_3$ are as follows:
$\omega_1$—water content, $\omega_2$—oil content and $\omega_3$—sand content.

4. The dual-energy x-ray measurement method of the constituent content in the three-phase mixture of claim 1, wherein when the three-phase mixture is a gas-water-sand three-phase mixture in the natural gas, the specific meanings of $\omega_1$, $\omega_2$ and $\omega_3$ are as follows:
$\omega_1$—water content, $\omega_2$—gas content and $\omega_3$—sand content.

5. The dual-energy x-ray measurement method of the constituent content in the three-phase mixture of claim 1, wherein the range of the energy $E_H^*$ of the high-energy x-ray machine is 10 keV-1 MeV, and the low-energy $E_L^*$ meets the relation formula: $E_H^* \approx (1.5\text{-}3) E_L^*$ or $E_H^* = 2E_L^*$.

6. The dual-energy x-ray measurement method of the constituent content in the three-phase mixture of claim 1, wherein when one of $\omega_1$, $\omega_2$ and $\omega_3$ is equal to 0, such as $\omega_3 = 0$, the x-ray machine of the measurement system produces a single-energy x-ray energy spectrum, and the following formula is adopted to solve the percentage content $\omega_1$ of the component 1 and the percentage content $\omega_2$ of the component 2:

$$\omega_1 = \frac{\ln\left(\frac{kN_0}{N(x) - kcN_0}\right) - \left(\frac{\mu_2}{\rho_2}\right)x\rho}{\left(\frac{\mu_1}{\rho_1} - \frac{\mu_2}{\rho_2}\right)x\rho} \quad (9)$$

$$\omega_2 = 1 - \omega_1$$

In the formula; $\rho$ represents the actual density under the two-phase state in an oil pipe, $\rho_1$ represents the density of the pure component 1 under the conditions of the corresponding temperature, the pressure and the like in the actual oil pipe, and $\rho_2$ represents the density of the pure component 2 under the conditions of the corresponding temperature, the pressure and the like in the actual oil pipe; $\mu_1$ and $\mu_2$ respectively represent the linear attenuation coefficients of the pure component 1 and the pure component 2 under the corresponding equivalent ray energy; x represents the linear thickness of the measurement space of the measurement system; $N_0$ represents the count measured by the measurement system without the existence of any component in the pipe under the condition of the corresponding equivalent ray energy; $N(x)$ represents the count measured by the measurement system under the conditions of the corresponding measurement thickness and the equivalent ray energy; and k and c are correction coefficients respectively and solved by pre-measurement of an exponential decay curve together with $\mu_1$ and $\mu_2$.

7. A measurement system used for the measurement method of claim 1, wherein the measurement system consists of the following sub-systems: a production sub-system of single-energy or dual-energy (spectrum) x-rays, a detector sub-system composed of one or two sets of detectors, a controlling and data processing sub-system and an additional system for calibration of long-term stability of a beam flow of the x-ray machine.

8. The measurement system of claim 7, wherein the production sub-system of the dual-energy x-rays uses the x-ray machine to directly produce the x-rays with two energy spectra, the high-energy and low-energy x-rays adopt the alternate way for time division output, the x-ray machine is a true dual-energy x-ray machine sub-system, a first-line controlling unit (26) transmits high-energy and low-energy identification signals transmitted from the true dual-energy x-ray machine sub-system to a data processing computer (28), and the data processing computer (28) distinguishes the high-energy and low-energy data measured by the detectors (4) according to the identification signals.

9. The measurement system of claim 7, wherein the production sub-system of the dual-energy x-rays uses two single-energy x-ray machines to produce the high-energy and low-energy x-rays, and the first group of the detectors (4) and the second group of the detectors (8) are used for measuring the high-energy and low-energy data.

10. The measurement system of claim 7, wherein the production sub-system of the dual-energy x-rays uses one single-energy x-ray machine to produce the high-energy and low-energy x-rays in a time division manner through a time division prehardening device, the x-ray machine is a pseudo dual-energy x-ray machine sub-system, the first-line controlling unit (26) transmits high-energy and low-energy identification signals transmitted from the pseudo dual-energy x-ray machine sub-system to the data processing computer (28), and the data processing computer (28) distinguishes the high-energy and low-energy data measured by the detectors (4) according to the identification signals.

11. The measurement system of claim 7, wherein the production sub-system of the dual-energy x-rays uses two single-energy x-ray machines which are installed in different positions to produce the high-energy and low-energy x-rays; the installation of the core parts of measurement equipment (1) of the measurement system adopts the transverse installation way of the two single-energy x-ray machines and the detectors, and two corresponding sets of detection passages are positioned on the same cross section of a crude oil pipeline (10) for reducing the length of the measurement equipment (1); and the range of the included angle θ between the two sets of the detection passages is as follows: $0°<\theta<180°$.

12. The measurement system of claim 7, wherein the single-energy x-rays are produced by one x-ray machine, the x-rays with two energy spectra are realized by the detector sub-system consisting of two sets of the detectors, the high-energy x-rays are obtained by prehardening one line of detectors, the low-energy x-rays are measured by the other line of the detectors, the measurement system is the pseudo dual-energy detector measurement system, and the data processing computer (28) carries out processing according to the high-energy and low-energy data measured by the first group of the detectors (4) and the second group of the detectors (8) of the pseudo dual-energy detector group.

13. The measurement system of claim 7, wherein the x-rays with two energy spectra are realized by the detector sub-system consisting of two sets of the detectors, and two lines of the detectors applying the prehardening technology to detect the high-energy and low-energy x-rays are made into a whole pseudo dual-energy detector; and the data processing computer (28) carries out processing according to a model algorithm provided in claim 1 based on the high-energy and low-energy data measured by the pseudo dual-energy detector.

14. The measurement system of claim 7, wherein the additional system for the calibration of the long-term stability of the beam flow of the x-ray machine is provided with a brightness correction detector I (33) or a detector II (38) at an outlet of each x-ray machine; the brightness correction detector is in the position of the outlet of the x-ray machine and deviates from a main beam flow for measurement, and the real-time calibration is carried out on the dose change of the x-ray machine based on the data measured by the brightness correction detector I (33) or the detector II (38), thereby eliminating the measurement error caused by the dose change of the x-ray machine.

\* \* \* \* \*